(12) United States Patent
Boitnott

(10) Patent No.: US 10,190,958 B2
(45) Date of Patent: Jan. 29, 2019

(54) PROBE PERMEAMETRY ON UNCONSOLIDATED FORMATIONS

(71) Applicant: New England Research, Inc., White River Junction, VT (US)

(72) Inventor: Gregory N. Boitnott, Hanover, NH (US)

(73) Assignee: New England Research, Inc., White River Junction, VT (US)

( * ) Notice: Subject to any disclaimer, the term of this patent is extended or adjusted under 35 U.S.C. 154(b) by 197 days.

(21) Appl. No.: 15/215,700

(22) Filed: Jul. 21, 2016

(65) Prior Publication Data

US 2017/0023462 A1    Jan. 26, 2017

Related U.S. Application Data

(60) Provisional application No. 62/196,497, filed on Jul. 24, 2015.

(51) Int. Cl.
*G01N 15/08* (2006.01)

(52) U.S. Cl.
CPC ....... *G01N 15/0826* (2013.01); *G01N 15/082* (2013.01)

(58) Field of Classification Search
None
See application file for complete search history.

(56) References Cited

U.S. PATENT DOCUMENTS

| | | | | |
|---|---|---|---|---|
| 2,713,789 | A * | 7/1955 | Kelton | G01N 15/0826 73/38 |
| 4,608,859 | A * | 9/1986 | Rockley | E21B 49/005 73/152.05 |
| 4,864,845 | A * | 9/1989 | Chandler | G01N 15/0826 702/12 |
| 5,237,854 | A * | 8/1993 | Jones | G01N 15/0826 73/38 |
| 5,878,374 | A * | 3/1999 | Buchanan | B01D 37/04 702/45 |

\* cited by examiner

*Primary Examiner* — Jill E Culler
(74) *Attorney, Agent, or Firm* — Richard A. Fagin

(57) ABSTRACT

A method for measuring permeability of a formation using a probe permeameter includes confining a sample of the formation in a container. The sample is covered with a screen having at least one perforation therein. The probe permeameter is applied to the at least one perforation in the screen. Permeability of the formation is measured at the at least one perforation.

6 Claims, 5 Drawing Sheets log [ Permeability mD ]

1.0                          4.0

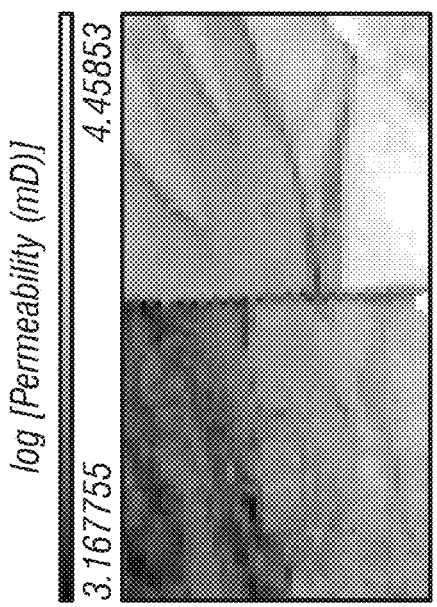
*FIG. 7C*
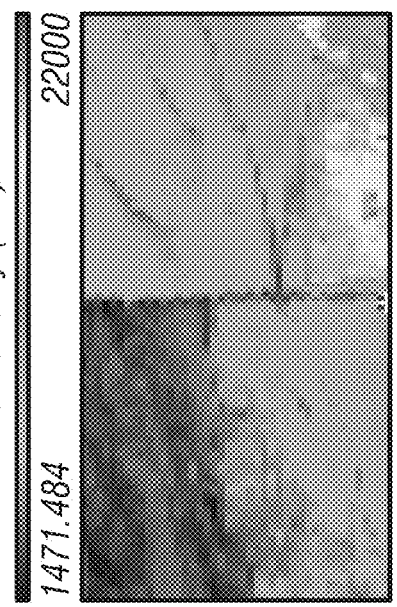
*FIG. 7D*
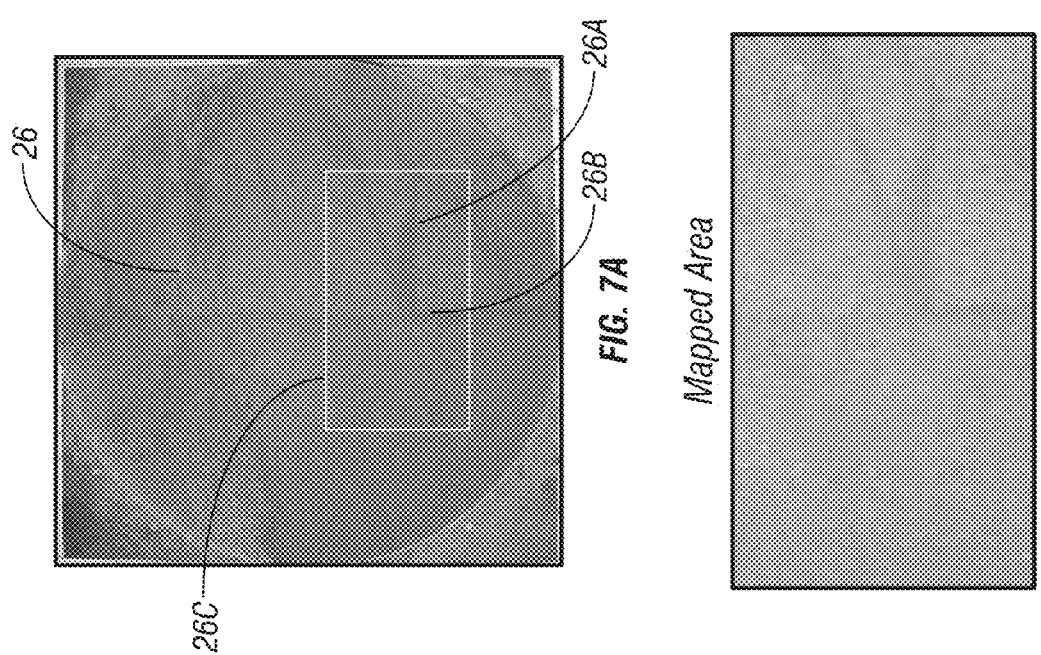
*FIG. 7A*
*FIG. 7B*

US 10,190,958 B2

PROBE PERMEAMETRY ON UNCONSOLIDATED FORMATIONS

CROSS REFERENCE TO RELATED APPLICATIONS

Priority is claimed from U.S. Provisional Application No. 62/196,497 filed on Jul. 24, 2015, which application is incorporated herein by reference in its entirety.

STATEMENT REGARDING FEDERALLY SPONSORED RESEARCH OF DEVELOPMENT

The invention disclosed herein was made in part pursuant to contract no. DE-FG07-02ER63497 with the United States Department of Energy. The United States Government retains certain rights to the invention.

NAMES TO THE PARTIES TO A JOINT RESEARCH AGREEMENT

Not Applicable.

BACKGROUND

This disclosure relates generally to the field of permeability determination of earthen formations. More specifically, the disclosure relates to probe type permeability determination in relatively unconsolidated formations.

Probe permeametry has proven to be a nondestructive, repeatable, and efficient method for measuring fine-scale variations in the permeability of earthen formations such as reservoir rocks. However, there are several technical challenges to the use of standard probe permeametry methods being directly applied to unconsolidated earthen formations. First, there is the problem of probe tip sealing force. When the probe tip seal is brought into contact with a formation sample surface, some axial force must be applied to the probe to compress the probe-tip seal and prevent fluid leakage at the interface between the probe tip and the formation sample. Unconsolidated samples lack the cohesion and strength required to resist the tip sealing force, which results in destructive compaction or displacement of rock grains when the probe tip comes into contact with the sample. Second, unconsolidated earthen formations are also difficult to prepare for probe permeametry, which often results in an uneven formation sample surface. An uneven formation sample surface may make it difficult to obtain a good seal between the probe tip and the formation sample.

Third, there are problems associated with the excavation and movement of small size (fine) rock grains within the formation sample. Even though fluid flowing through the formation samples during permeametry is only moderately pressurized, because such formation samples have high permeabilities the fluid flow rate can be high enough to overcome the cohesive and inertial forces in the formation sample and forcibly expel fine grains from the formation sample. Such movement of fine grains permanently alters the formation sample and results in permeability measurements that do not reflect the true permeability of the formation prior to structural alteration caused by mechanisms such as those described above.

BRIEF DESCRIPTION OF THE DRAWINGS

FIG. 7A shows an image of a more massive sample with a vertically oriented through-going fault.

FIG. 7B shows the measured area of the sample in FIG. 7A.

FIG. 7D shows a permeability map of the measured area of FIG. 7B.

FIG. 7C shows the logarithm of the permeability map of FIG. 7D in black and white for higher contrast.

DETAILED DESCRIPTION

Example methods according to the present disclosure may enable accurate probe permeability measurements on unconsolidated formation samples. The methods include the use of a perforated screen as an interface between the permeability probe and the formation sample surface. Example methods according to the present disclosure have been tested, and have calibrated the probe and screen combination using synthetic formation samples and assuming that the permeability of unconsolidated formation materials follows the Kozeny-Carman relationship. Tests have also been performed on natural earthen formation samples, illustrating the effectiveness of the procedure.

Test probe permeametry measurements were made using a core scanning platform sold under the trademark AUTOSCAN II, which is a trademark of New England Research Inc., White River Jct., Vt. The AUTOSCAN II scanning platform is an integrated platform consisting of a software controlled robotic gantry that allows automatic positioning of a probe or other device on an integrated table in precise coordinates, e.g., Cartesian (X-Y) coordinates.

Samples of unconsolidated earthen formations were covered with a layered, perforated screen that was capable of providing structural support to the formation sample, a good seal between the permeametry probe tip seal and the formation sample, while being "transparent" to the permeability probe.

Figure 1:
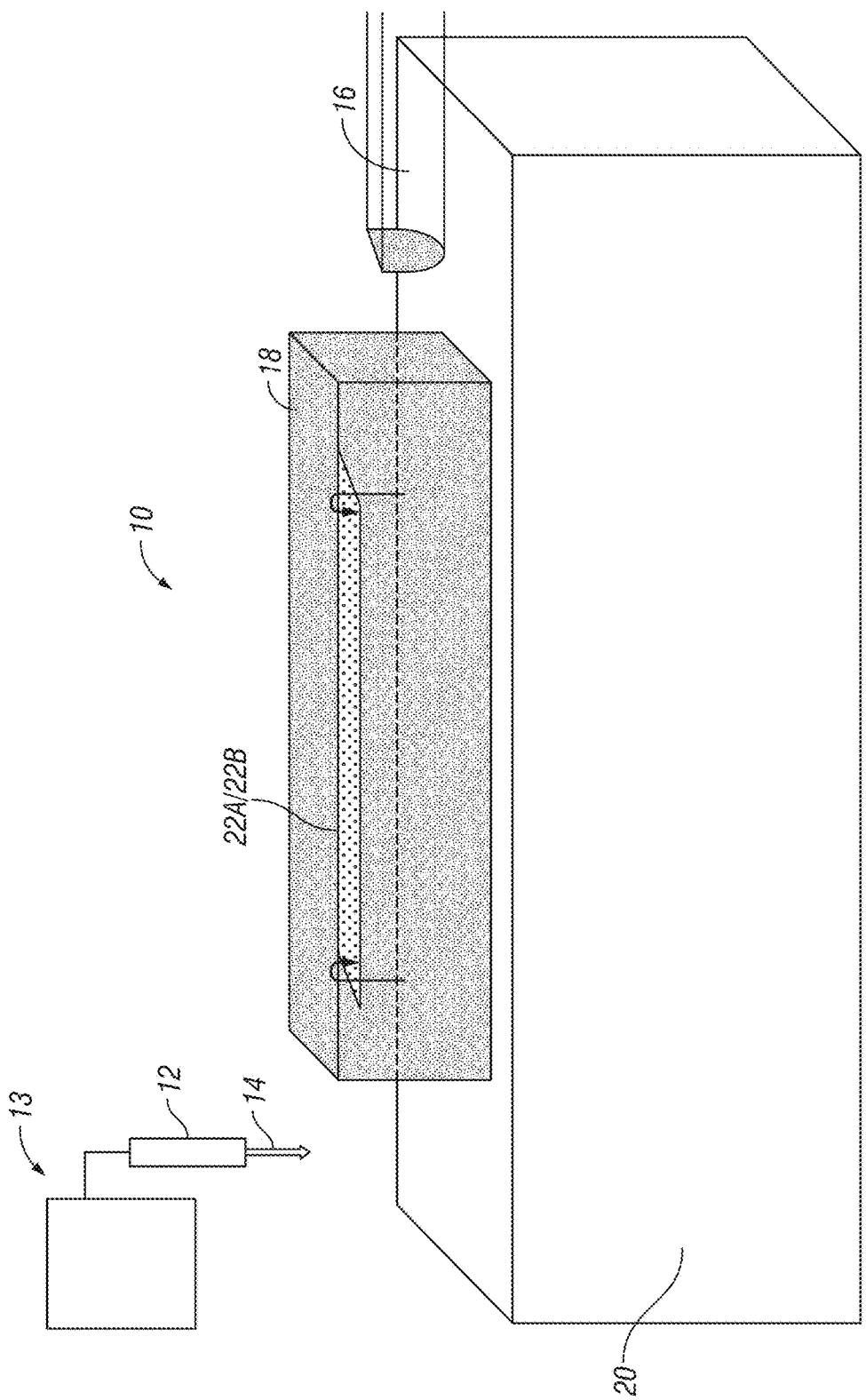
FIG. 1 shows a schematic diagram of a probe permeameter making measurements according to the present disclosure.

FIG. 1 schematically shows measurement of permeability using a probe permeameter system 10 such as may be used with the AUTOSCAN II scanning platform described above. A scanner table is shown at 20. A scanner robotic gantry is shown schematically at 12. A permeameter probe tip is shown at 14. A formation sample, such as a core sample 16 may be moved into a retaining enclosure, container or box 18 disposed on the scanner table 20. A perforated elastomer membrane 22A, such as a rubber membrane, covered by a correspondingly perforated screen 22B may be applied over the surface of the core sample 16 and held in place, e.g., by clamps (not shown). Permeability measurements may be made at selected positions about the surface of the core sample 16, e.g., by pumping fluid into the core sample 16 through the permeameter probe tip 14. It may be desirable for the perforated screen 22B, which may be better described as a perforated sheet, be made from slightly flexible material such as plastic and have thickness selected such that the perforated screen 22B enables transmission of some of the axial force applied by the permeameter probe tip 14 preferentially in area of contact between the probe tip 14 and the perforated screen 22B and between the perforated screen 22B and the core sample 16 to ensure a fluid tight seal between the permeameter probe tip 14 and the core sample 16.

The permeameter probe tip 14 may be functionally coupled to a permeameter system 13 of types well known in the art. One non-limiting example of a permeameter system is sold under model designation PPP-250 by Core Laboratories, Inc., 4616 North Mingo, Tulsa, Okla. 74117.

Because formation samples themselves are not perfectly smooth and rigid, it may be desirable that the perforated screen 22B has a rigidity (e.g., determined by the mechanical properties of the screen material and the thickness of the perforated screen 22B) selected to enable the perforated screen 22B to deform sufficiently to maintain contact with the core sample 16 given irregularities in the surface of the core sample 16, while distributing the axial force exerted by the permeameter probe tip 14 well enough so as not to deform the surface of the core sample 16 when the permeameter probe tip 14 sealingly engages the perforated screen 22B.

Figure 2:
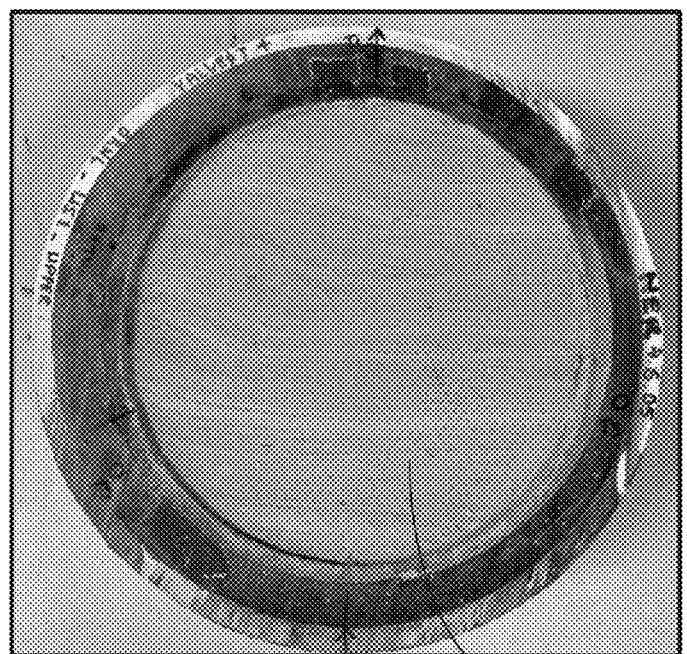
FIG. 2 shows a surface of a core sample prior to application of a perforated elastomer membrane.
Figure 3:
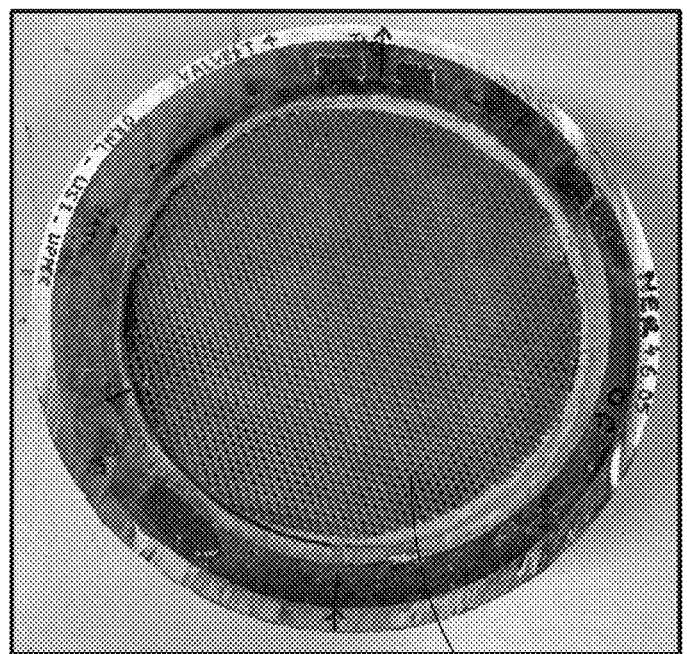
FIG. 3 shows the core sample of FIG. 2 after application of a perforated elastomer membrane.
Figure 4:
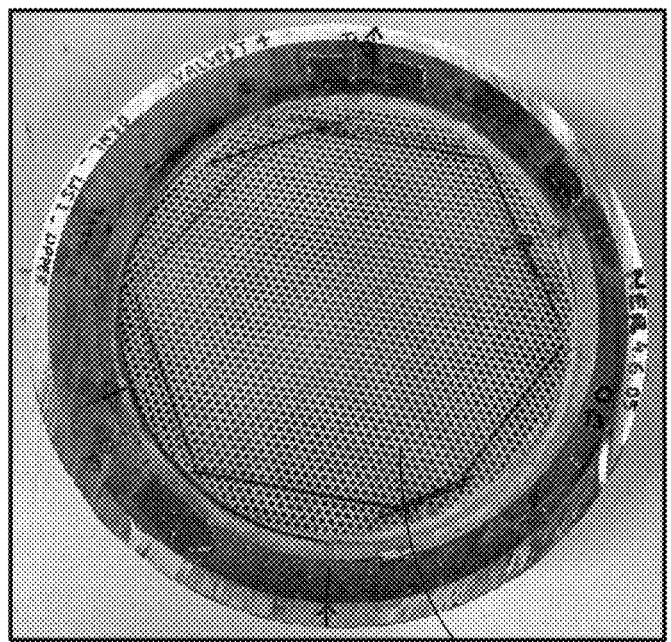
FIG. 4 shows the core sample of FIG. 3 after application of a perforated screen above the elastomer membrane.

FIGS. 2, 3 and 4 show, respectively, the surface of a core sample 16, the core sample 16 covered by a perforated elastomer membrane 22A, such as a rubber membrane and subsequently covered by a correspondingly perforated screen 22B, such as a metal screen.

In order to measure quantitative differences in permeability using a small permeameter probe tip, measurements were made on synthetic samples made from aluminum oxide grinding powders. Measured permeability was compared with permeability values predicted from the Kozeny-Carman equation. The Kozeny-Carman equation can be written in terms of percolation porosity and grain size as follows:

$$K = \frac{B(\phi - \phi_c)^3}{(1 + \phi_c - \phi)^2} d^2,$$

where K is permeability, B is a geometric factor, d is characteristic grain size, $\phi$ is porosity, and $\phi_c$ is the percolation porosity. For unconsolidated sandstone formations, B is approximately 15, $\phi_c$ is approximately 3.5%. See, Mavko, G., Mukerji, T. and Dvorkin, J., *The Rock Physics Handbook*, Cambridge University Press, Cambridge, United Kingdom, 1998. For synthetic formation samples, $\phi$ was determined using the density method.

Figure 5:
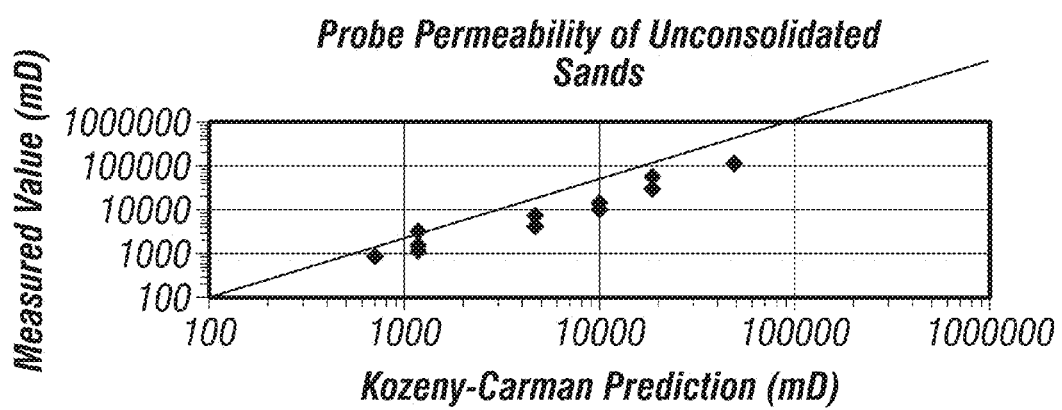
FIG. 5 shows a graph of permeability tests on synthetic samples with theoretical permeability given by the Kozeny-Carman equation.

Results from the calibration experiments are shown in FIG. 5. Good agreement is observed over a wide range of grain size mixtures. Measured permeabilities are in general systematically greater than the Kozeny-Carman equation predicted values by about a factor of 2, however it is believed that this discrepancy is within the uncertainty in the parameter B, which for the calibration experiments a typical value from literature was used.

Methods according to the present disclosure were tested on unconsolidated formation samples from a glacial kame terrace of Pleistocene age. Kame terraces are typically sand and gravel deposits, formed by the actions of met-water streams flowing along the sides of glacial ice and trapped by valley walls. These deposits are comprised of unconsolidated clays, silts, sands, and gravels and provide the opportunity to study multi-scale sedimentary structures. There are also many joints and faults in this unconsolidated material, allowing sampling and study of these as either potential fluid flow conduits or barriers.

Figure 6A:
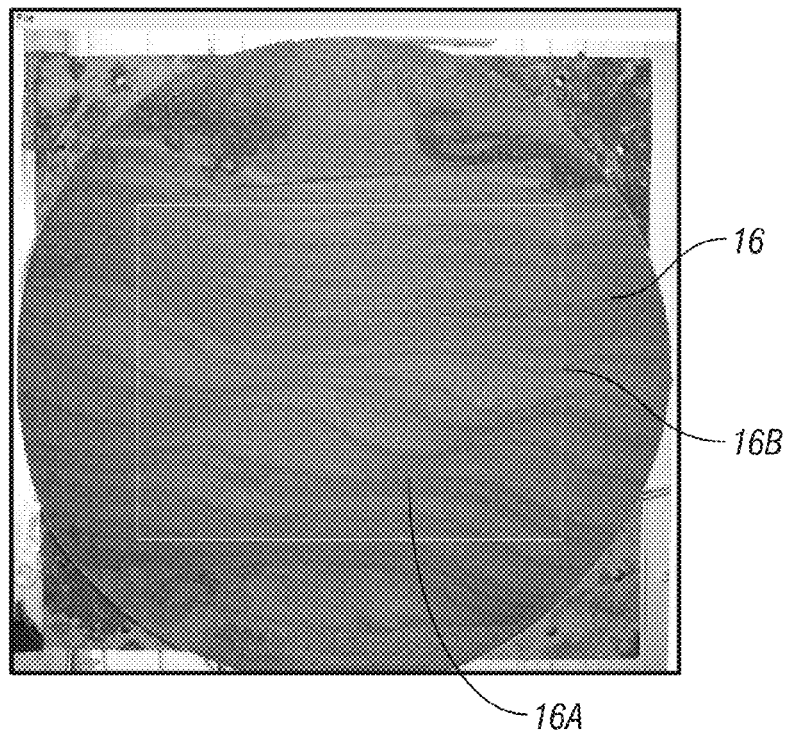
FIG. 6A shows an unconsolidated sample from a glacial kame terrace of Pleistocene age.
Figure 6B:
FIG. 6B shows a permeability map of a denoted area of the sample of FIG. 6 made using measurements according to FIG. 1.

FIG. 6A shows a visual image of a core sample 16 with a testing area 16A highlighted by a white box 16B. Note the extensive crossbedding of layered fine-grained sands interrupted by thin, clay-rich layers. Also note that the layering sequence changes character at the top of the core sample 16, starting with a series of finely interbedded sand and clay layers and ending at the top of the core sample 16 with several thicker clay-rich layers. The corresponding permeability map of the testing area 16A made using the apparatus shown in FIG. 1 is shown in FIG. 6B. Measurements were made through the previously described perforated screen (22B in FIG. 4) on a hexagonal grid corresponding to the selected hole spacing of the perforated screen (22B in FIG. 4). The hole spacing appears to provide enough resolution to image all of the crossbedded structure, even the finer interbedded layers. Measured gas permeability spans three orders of magnitude, with the highest measured permeabilities occurring in the coarser sand layers at the bottom of the core sample 16, and the lowest measured permeabilities found in the clay-rich layers located at the top of the core sample 16. The spatial distribution of permeability is somewhat intuitive, as the permeability appears to be strongly correlated with grain size.

In some embodiments the holes in the membrane (22A in FIG. 3) and the perforated screen (22B in FIG. 4) may be substantially the same diameter as the diameter of the permeameter probe tip (14 in FIG. 1). Such size selected enables fluid flow into the formation sample through a single perforation that is large enough that the holes in the membrane and the screen do not appreciably restrict the flow of fluid into the sample. In such embodiments, the spacing between adjacent holes in the membrane (22A in FIG. 3) and the perforated screen (22B in FIG. 4) may be selected such that holes adjacent to the particular hole being tested are sufficiently close and in sufficient numbers to allow the test fluid to escape the sample evenly enough so as to not appreciably restrict the flow.

In other words, the geometry of the holes in the membrane and the perforated screen may be such that the flow of test fluid is minimally different from what it would have been if the sample were strong enough to be measured without the membrane and screen in place. In some embodiments it may be desirable to add a porous filter in each of the holes in the membrane and/or the perforated screen to keep the flow of fluid from dislodging mineral grains in the sample.

FIG. 7A shows an image of a more massive sample 26 with a vertically oriented through-going fault shown at 26B. Note the iron staining in the lower right corner of the sample that does not continue across the fault 26B, implying that the fault 26B is a barrier to fluid flow. The tested area is shown at 26B and is outlined by the white box. FIG. 7B shows the tested area. FIG. 7D shows an image of the corresponding probe permeability map. There are two major features to note. First, the fault appears as a low permeability feature, confirming the visual observation that it is a fluid flow barrier. Second, the probe permeameter reveals significant structures in the visually massive sand, such as the local permeability high in the lower right hand corner of the sample. This observation illustrates how the probe permeametry can be used to identify sedimentary structures and facies that are difficult to recognize by simple visual analysis.

FIG. 7C shows a logarithmic gray scale version of the permeability map for better visual contrast.

Methods according to the present disclosure may provide accurate probe permeability measurements in unconsolidated formations by reducing structural changes in the formations as a result of forces applied by the probe and movement of the permeability measuring fluid through the formations (which may cause migration of fine grained particles).

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for measuring permeability of a formation using a probe permeameter, comprising:
    confining a sample of the formation in a container;
    covering the formation sample with a screen having a plurality of perforations therein, the screen being configured to conform to irregularities in a surface of the formation sample;
    applying the probe permeameter to at least one selected perforation in the screen, wherein the screen distributes a load from the probe permeameter sufficiently so as not to deform the sample and thereby provides a fluid tight seal between probe tip and the formation sample; and measuring permeability of the formation at the at least one selected perforation.

2. The method of claim 1 further comprising applying an elastomer membrane between the formation sample and the screen, the elastomer membrane having perforations corresponding to the perforations in the screen.

3. The method of claim 1 wherein a diameter of the perforations is substantially equal to a diameter of a tip on the probe permeameter.

4. The method of claim 1 wherein a spacing between the perforations is selected such that flow of test fluid through the formation sample is substantially the same as would occur without the membrane and screen.

5. The method of claim 1 further comprising moving the permeameter probe to a position of a different perforation in the perforated screen and repeating the applying the probe permeameter and measuring permeability at the position of the different perforation.

6. The method of claim 5 further comprising:
    repeating the moving the permeameter to a different perforation position, the applying the permeameter to the different perforation and measuring permeability to a plurality of different perforations within a defined area on a surface of the formation sample; and
    generating an image based on the measured permeability at the plurality of different perforations within the defined area.

* * * * *